(12) United States Patent
Kennedy et al.

(10) Patent No.: US 9,901,658 B2
(45) Date of Patent: Feb. 27, 2018

(54) METHOD FOR THE PRODUCTION OF POLY(2-OCTYL CYANOACRYLATE)-POLYISOBUTYLENE CO-NETWORK, AND SUPER INITIATORS THEREFOR

(71) Applicants: Joseph Kennedy, Akron, OH (US); Istvan Szanka, Balmazujvaros (HU); Amalia Szanka, Budapest (HU)

(72) Inventors: Joseph Kennedy, Akron, OH (US); Istvan Szanka, Balmazujvaros (HU); Amalia Szanka, Budapest (HU)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

(21) Appl. No.: 15/302,744

(22) PCT Filed: Oct. 21, 2014

(86) PCT No.: PCT/US2014/061528
§ 371 (c)(1),
(2) Date: Oct. 7, 2016

(87) PCT Pub. No.: WO2015/175014
PCT Pub. Date: Nov. 19, 2015

(65) Prior Publication Data
US 2017/0028099 A1    Feb. 2, 2017

Related U.S. Application Data
(60) Provisional application No. 61/992,954, filed on May 14, 2014.

(51) Int. Cl.
*C08F 22/32* (2006.01)
*A61L 24/06* (2006.01)
(Continued)

(52) U.S. Cl.
CPC .............. *A61L 24/06* (2013.01); *C08F 22/32* (2013.01); *C08F 265/08* (2013.01);
(Continued)

(58) Field of Classification Search
CPC .... A61L 2430/34; C08F 22/32; C08G 83/003
See application file for complete search history.

(56) References Cited

U.S. PATENT DOCUMENTS 3,260,637 A * 7/1966 Von Bramer ........... C08F 22/30
                                                    156/314
7,341,716 B2   3/2008 Porter
(Continued)

FOREIGN PATENT DOCUMENTS

WO    WO 2012109179 A2 *  8/2012 .............. C08F 22/32

OTHER PUBLICATIONS

Katti et al. Journal of Applied Polymer science vol. 74, 336-344 1999.*

*Primary Examiner* — Mark S Kaucher
(74) *Attorney, Agent, or Firm* — Renner Kenner Greive Bobak Taylor & Weber

(57) ABSTRACT

A method for increasing the rate of polymerization of 2-octyl cyanoacrylate, or the rate of copolymerization of 2-octyl cyanoacrylate and a tri-telechelic star polymer comprising polyisobutylene terminated with cyanoacrylate groups (Ø(PIB-CA)$_3$) to form a co-network, is provided. The method comprise initiating the polymerization of 2-octyl cyanoacrylate, or the copolymerization of 2-octyl cyanoacrylate and a tri-telechelic star polymer comprising polyisobutylene terminated with cyanoacrylate groups (Ø(PIB-CA)$_3$) to form the co-network, with an initiator selected from the group consisting of cyclic tertiary aliphatic amines optionally dissolved in a non-aqueous solvent. The cyclic tertiary aliphatic amines are selected from the group con- (Continued)

sisting of azabicyclo[2.2.2]-octane (ABCO), and 1,4-diazabicyclo[2.2.2]-octane (DABCO).

13 Claims, 10 Drawing Sheets

(51) Int. Cl.
    *C08F 265/08*     (2006.01)
    *C08F 279/02*     (2006.01)
    *C08G 83/00*     (2006.01)

(52) U.S. Cl.
    CPC .......... *C08F 279/02* (2013.01); *C08G 83/003* (2013.01); *A61L 2430/34* (2013.01)

(56) References Cited

U.S. PATENT DOCUMENTS

| | | |
|---|---|---|
| 2008/0243082 A1 | 10/2008 | Goodman |
| 2009/0264566 A1 | 10/2009 | Schambony et al. |
| 2010/0144996 A1* | 6/2010 | Kennedy ................. A61L 27/16 526/310 |
| 2010/0172858 A1* | 7/2010 | Jegou ....................... A61K 8/40 424/70.16 |
| 2014/0073743 A1 | 3/2014 | Kennedy et al. |

* cited by examiner

Polymerization of Oc-CA with DMT in Bulk

| 2-octyl cyanoacrylate | | DMT | $[M]_0/[I]_0$ | Gel time |
|---|---|---|---|---|
| mmol | g | mmol | | sec |
| 9.53 | 1.9950 | 0.0173 | 550 | 396 |
| 7.22 | 1.5118 | 0.0173 | 420 | 335 |
| 4.75 | 0.9936 | 0.0173 | 270 | 254 |
| 4.85 | 1.0154 | 0.0346 | 140 | 168 |
| 4.83 | 1.0105 | 0.0693 | 70 | 105 |
| 4.81 | 1.0063 | 0.1386 | 35 | 66 |
| 4.85 | 1.0144 | 0.2079 | 23 | 50 |

FIG. 6

Polymerization of Oc-CA with ABCO dissolved in THF

| 2-octyl cyanoacrylate | | ABCO | THF in syst. | $[M]_0/[I]_0$ | Gel time |
|---|---|---|---|---|---|
| mmol | g | mmol | vol.% | | sec |
| 4.69 | 0.9811 | 2.15E-04 | 5 | 21800 | 184 |
| 3.71 | 0.7759 | 2.15E-04 | 6 | 17200 | 135 |
| 3.07 | 0.6422 | 2.15E-04 | 8 | 14300 | 101 |
| 4.87 | 1.0189 | 4.30E-04 | 9 | 11300 | 57 |
| 3.97 | 0.8315 | 4.30E-04 | 11 | 9200 | 42 |

FIG. 7

Polymerization of Oc-CA with DABCO dissolved in THF

| 2-octyl cyanoacrylate | | DABCO | THF in syst. | $[M]_0/[I]_0$ | Gel time |
|---|---|---|---|---|---|
| mmol | g | mmol | vol.% | | sec |
| 5.63 | 1.1778 | 2.58E-04 | 4 | 21800 | 253 |
| 4.90 | 1.0263 | 2.58E-04 | 5 | 19000 | 185 |
| 3.84 | 0.8044 | 2.58E-04 | 6 | 14900 | 124 |
| 3.23 | 0.6752 | 2.58E-04 | 7 | 12500 | 100 |
| 5.05 | 1.0574 | 5.16E-04 | 9 | 9800 | 56 |
| 4.00 | 0.8379 | 5.16E-04 | 11 | 7800 | 36 |

FIG. 8

Polymerization of Oc-CA with ABCO dissolved in Toluene

| 2-octyl cyanoacrylate | | ABCO | Toluene in | $[M]_0/[I]_0$ | Gel time |
|---|---|---|---|---|---|
| mmol | g | mmol | syst. vol.% | | sec |
| 4.86 | 1.0168 | 9.60E-04 | 17 | 5100 | 248 |
| 4.81 | 1.0066 | 9.60E-04 | 17 | 5000 | 198 |
| 2.41 | 0.5051 | 4.80E-04 | 17 | 5000 | 220 |
| 3.76 | 0.7863 | 9.60E-04 | 21 | 3900 | 194 |
| 2.87 | 0.6015 | 9.60E-04 | 26 | 3000 | 124 |
| 3.54 | 0.7402 | 1.44E-03 | 30 | 2500 | 100 |
| 4.91 | 1.0268 | 4.80E-04 | 9 | 10200 | 338 |
| 3.61 | 0.7545 | 4.80E-04 | 12 | 7500 | 268 |

FIG. 9

Polymerization of Oc-CA with DABCO dissolved in Toluene

| 2-octyl cyanoacrylate | | DABCO | Toluene in | $[M]_0/[I]_0$ | Gel time |
|---|---|---|---|---|---|
| mmol | g | mmol | syst. vol.% | | sec |
| 4.79 | 1.0023 | 4.20E-04 | 9 | 11400 | 417 |
| 4.89 | 1.0239 | 4.20E-04 | 9 | 11600 | 419 |
| 3.90 | 0.8153 | 4.20E-04 | 11 | 9300 | 335 |
| 2.84 | 0.5945 | 4.20E-04 | 15 | 6800 | 244 |
| 2.41 | 0.5046 | 4.20E-04 | 17 | 5700 | 195 |
| 1.97 | 0.4133 | 4.20E-04 | 20 | 4700 | 169 |

METHOD FOR THE PRODUCTION OF POLY(2-OCTYL CYANOACRYLATE)-POLYISOBUTYLENE CO-NETWORK, AND SUPER INITIATORS THEREFOR

CROSS REFERENCE TO RELATED APPLICATIONS

This application claims the benefit of U.S. Provisional Patent Application No. 61/992,954, filed May 14, 2014, the disclosure of which is hereby incorporated by reference.

TECHNICAL FIELD

This invention relates to a method for the production of a polyisobutylene-based co-network and, more particularly, to a method for increasing the rate of copolymerization for making a poly(2-octyl cyanoacrylate)-polyisobutylene co-network. Further, the invention relates to the preparation and use of new initiator compounds suitable for initiating the copolymerization of the reactants for making the co-network.

BACKGROUND OF THE INVENTION

There is a great need in biomedical applications, including orthopedic practice, for sealants or adhesives of wounds and surgical cuts. Such sealants contemplated could range from sealants used for wound healing and wound closure on the skin to sealants used to permanently seal scalpel cuts and puncture wounds made by large bore injection needles in the course of various procedures.

At present, there is no satisfactory orthopedic sealant being used to satisfy the need for closing iatrogenic defects made in the annulus fibrosa during discectomies. This can cause serious problems in that the intervertebral disc may subsequently undergo accelerated degeneration, and the patient may require a spinal fusion some years later. Some implants have been proposed to resolve the issue but these were introduced without biomechanical considerations. Mechanical barriers have been recently proposed but are fundamentally different from an annulus sealant in that it (1) lacks the ability to reconstruct the annulus directly and restore motion, (2) cannot prevent the leakage of smaller particles from within the nucleus pulposus, (3) is more technically difficult to employ, and (4) would carry a significant risk of neurologic injury if extruded into the canal. No long term data is available on these products.

Further, there is also an unmet need for more flexible wound closure adhesives on the surface of the skin. Currently known wound closure adhesives include 2-octyl-cyanoacrylate (Oct-CA), known commercially by the brand name Dermabond®, available from Ethicon US LLC, a Johnson & Johnson company, wherein Dermabond® is a registered trademark of Johnson & Johnson Company, New Brunswick, N.J., and N-butyl-2-cyanoacrylate, known commercially by either Indermil® tissue adhesive, available from Covidien Co., a Henkel company, wherein Indermil® is a registered trademark of Henkel Corporation, Rocky Hill, Conn., or Histoacryl® topical skin adhesive, available from B. Braun Corporation, wherein Histoacryl® is a registered trademark of Aesculap, Inc., Center Valley, Pa. That is, it is well known that these monomers readily polymerize upon exposure to traces of moisture on surfaces such as skin. The CA group in these compounds is highly reactive toward nucleophiles because of the presence of the two highly electron withdrawing substituents (CN— and COO—), so that CA polymerizations are initiated by moisture. For instance, lower alkyl CAs such as methyl cyanoacrylates or ethyl cyanoacrylate (Superglue®) instantaneously polymerize in the presence of surface moisture. The rates of polymerizations are notably lower with the higher alkyl CAs (e.g., Oct-CA) due to the lower molar concentration of the CA groups.

Accordingly, a need exists to increase the rate of polymerization of these higher alkyl CAs (e.g., Oct-CA) without introducing any lower alkyl CAs, since the lower alkyl CAs are known to have toxicity concerns and cannot be used inside the body, but yet provide increase flexibility upon polymerization and higher viscosity than is normally available using commercially available wound closures containing 2-octyl-cyanoacrylate (Oct-CA) as the active ingredient. That is, commercial products such as Dermabond® are known to exhibit undesirably low viscosity (i.e., too runny) and to exhibit undesirable stiffness upon production (i.e., the coatings produced are too stiff and have low tensile strength).

More recently, and to overcome at least the stiffness problem, homopolymer networks containing cyanoacrylate-functionalized multi-arm polyisobutylene stars have been employed to provide more flexibility and rubberyness. These homopolymer networks have been developed and patented. The production of such polyisobutylenes provide for a core (Ø) with a desired number of polyisobutylene arms extending therefrom.

There are many potential biomedical applications with polyisobutylene with attachment of various polymers at the end of each arm. One clinical example where polyisobutylene has been adopted is poly(styrene-b-isobutylene-b-styrene), which is currently used as a coating in the Taxus® Drug Eluting Stent. Another potential application is for all applications where 2-octyl cyanoacrylate (Dermabond®) is currently employed and more flexibility is required.

To that end, cyanoacrylate-telechelic three-arm star polyisobutylenes have been prepared. Cyanoacrylate-telechelic three-arm star polyisobutylenes, Ø(PIB-CA)$_3$, were first prepared in 1991. A low viscosity syringible and injectable homopolymer functionalized with ethyl cyanoacrylate (i.e., Et-CA) was subsequently developed in 2007. It was found that a bolus of covalently linked PIB rubber "superglue" was created when Ø(PIB-CA)$_3$ was injected into (egg) protein and the properties could be controlled by addition of polyethyl-2-cyanoacrylate. On its own, Ø(PIB-CA)$_3$ has a tensile strength of 1.6 MPa, Young's Modulus of 4.9 MPa, and an elongation of 70%. Comparatively, the tensile strength of clinically available 2-octyl cyanoacrylate based "superglue", Dermabond® (Ethicon, J&J) and SurgiSeal™ (Adhezion Biomedical), is less than 0.1 MPa.

Furthermore, it was found that cyanoacrylate-ended tritelechelic polyisobutylene Ø(PIB-CA)$_3$ (Mn~2500 g/mol or more) are nontoxic in rats in vivo. Without being bound by theory, it is believed that the biocompatible high barrier rubbery PIB moiety effectively envelops and shields the noxious cyanoacrylate groups from the surrounding tissue and the permanently sequestered -CA groups are rendered harmless. However, too high molecular weight Ø(PIB-CA)$_3$ could also render the benefit of the —CA groups useless as well, as the rate of polymerization would be greatly slowed.

As noted above, it took several years for the production of a co-network of Ø(PIB-CA)$_3$ and Et-CA. This is because Et-CA is not miscible with Ø(PIB-CA)$_3$. It was only by way of mechanical means (i.e., a dual injectable syringe) that the two components could be brought into contact with each other at a particular site for use. Moreover, the amount and molecular weight of Et-CA was such that only small amounts could be used. Accordingly, the result was the production of a homopolymer network wherein the Et-CA was considered simply a crosslinker. That is, the molar ratio of the Ø(PIB-CA)$_3$ to Et-CA was so high that the resultant product is today considered a network with a Et-CA crosslinker, rather than a co-network of Ø(PIB-CA)$_3$ and Et-CA. Thus, other alternative networks to Ø(PIB-CA)$_3$ and Et-CA were sought.

Even more recently, new co-networks consisting of Ø(PIB-CA)$_3$ and Oct-CA have been developed. Such co-networks have been found to provide the flexibility, elongation and tensile strength of Ø(PIB-CA)$_3$ with the "super-glue" properties of 2-octyl cyanoacrylates. The polymerization of simple alkyl cyanoacrylates, and specifically, 2-octyl cyanoacrylate (Oct-CA), with and in addition to the cyanoacrylate-functionalized three arm star polyisobutylenes, Ø(PIB-CA)$_3$, have been found to provide useful co-networks that may be desirable in a number of biomedical applications.

However, heretofore, the co-networks, have only been tested on moisture-provided surfaces such as skin. As such, known co-networks of poly(2-octyl cyanoacrylate) (Oct-CA) and tri-telechelic cyanoacrylate-functionalized polyisobutylene (Ø(PIB-CA)$_3$) have only been developed by way of initiation from moisture obtained from the surface to which it is applied. That is, the polymerization reaction was initiated by nucleophilic groups located on the surface to be covered by the co-network, such as, in one embodiment, skin. The co-network exhibited higher elongation than a homopolymer of octyl cyanoacrylate and exhibited strength sufficient to hold two pieces of skin together. However, when using only the skin or moisture from the surface covered as an initiator, the set time of the adhesive, i.e., the time the liquid wound closure adhesive (i.e., the co-network) takes to become a tack free solid after applying it to surfaces, is somewhat lengthy (i.e., much longer than 120 seconds— typically 6 to 10 minutes) compared to the set times preferred by doctors who would use the wound closure adhesives. Such preferred set times are in the 30-120 seconds range. Again, without being bound by theory, it is believed that the rate of polymerization is slowed due to the initiation of the polymerization via only the nucleophiles on the skin.

Therefore, the need exists for other co-networks formed by polymerizing tri-telechelic cyanoacrylate-functionalized polyisobutylene (Ø(PIB-CA)$_3$) and 2-octyl cyanoacrylate (Oct-CA) that are initiated, or rather, super initiated by methods other than from moisture on the surface to which they are being applied. While it may be possible or desirable to enhance the initiation process with the nucleophilic groups located on the surface (e.g, skin) covered by the poly co-network, the present invention seeks to use other initiation methods and other initiators, including novel initiators to provide improved co-networks of tri-telechelic cyanoacrylate-functionalized polyisobutylene (Ø(PIB-CA)$_3$) and 2-octyl cyanoacrylate (Oct-CA) for use in various biomedical applications such as wound closure adhesives.

One known initiator is N,N-dimethyl-p-toluidine (DMT), commercially available from Aldrich. DMT was used to initiate the polymerization of Ø(PIB-CA)$_3$ with ethyl cyanoacrylate to form the co-network. In practice, approximately 0.8 grams of Ø(PIB-CA)$_3$ was dissolved in 3 mL toluene, as a solvent, in a 10 mL test tube, and small amounts of Et-CA were added, followed by 1 drop (approximately 37 μmol) of DMT initiator. The solution was shaken and then poured into a 5×5 cm square Teflon mold, covered with aluminum foil, and the solvent was then evaporated in a fume hood for 2 days. Finally, the film was vacuum dried at 100° C. to constant weight and sol fractions were determined in THF.

To date, the use of DMT has been limited to initiation of Ø(PIB-CA)$_3$ with ethyl cyanoacrylate as a crosslinker. It has not been used to date in a physical co-network like the present invention. Even so, the need exists for new initiators (a) that do not require solvents, (b) that can be used for the polymerization of tri-telechelic cyanoacrylate-functionalized polyisobutylene (Ø(PIB-CA)$_3$) and 2-octyl cyanoacrylate (Oct-CA), and/or (c) that provide improvements in the mechanical properties.

Again, for skin, the active ingredient in commercially successful wound closure adhesives are alkyl cyanoacrylates (CAs), typically, butyl- or 2-octyl cyanoacrylate (Bu-CA, Oct-CA), marketed under a variety of trade names, such as Hystoacryl® and Dermabond®, respectively. The CA molecules, due to their strongly electron-withdrawing groups at unsaturations, rapidly polymerize upon contact with even the weakest of nucleophiles, such as water. Thus, the moisture on the skin may be sufficient in some cases to provide for the polymerization. However, that is not true for all cases.

Wound closure adhesives are usually packaged in special delivery devices, wherein the CA (together with a variety of additives, modifying agents, etc.) is sealed in a thin-walled glass vial that is crushed upon deployment, and the liquid monomer is forced toward the skin through a small porous plastic sponge (typically of polypropylene) situated at the tip of the delivery port.

It is not generally appreciated that this sponge performs two critical functions: (a) it helps delivering the active ingredient evenly over the targeted surface, and, more importantly, (b) it contains a key component, the initiator, which induces and accelerates the polymerization of the CA monomer as it is squeezed through the sponge. Absent the initiator, the set time is undesirably long, usually many minutes (i.e. 6 to 10 minutes).

The scientific literature mentions a large variety of initiators for the polymerization of alkyl CAs, e.g., water, bases, anions, methanol, amines, phosphines, and alkyl ammonium salts. However, the exact nature and concentrations of initiators used in commercial devices are closely guarded trade secrets. A search of the patent literature gave some insight as to the identity of initiators employed in practice for the polymerization of CAs in general and Oct-CA in particular, together with the nature of other ingredients (plasticizing agents, stabilizers, thickeners, etc.) dissolved in Oct-CA for commercial formulations to enhance the performance of these adhesives. However, it is readily apparent that the initiator of choice most often used to rapidly polymerize CAs, especially Oct-CA is DMT.

SUMMARY OF INVENTION

One or more of the following aspects, together with the advantages thereof over the known art relating to cyanoacrylate-based homopolymers and co-networks, which shall become apparent from the specification that follows, are accomplished by the invention as hereinafter described and claimed.

In general, the present invention provides a method for increasing the rate of polymerization of 2-octyl cyanoacrylate or the rate of copolymerization of 2-octyl cyanoacrylate and a tri-telechelic star polymer comprising polyisobutylene terminated with cyanoacrylate groups (Ø(PIB-CA)$_3$) to form a co-network. The method comprises initiating the polymerization of 2-octyl cyanoacrylate or the copolymerization of 2-octyl cyanoacrylate and Ø(PIB-CA)$_3$ with an initiator selected from the group consisting of cyclic tertiary aliphatic amines optionally dissolved in a non-aqueous solvent.

The method is particularly directed to the use of the cyclic tertiary aliphatic amines. In one embodiment, it is to be noted that these tertiary amines are not aromatic tertiary amines. More particularly, these cyclic tertiary aliphatic amines are selected from the group consisting of azabicyclo [2.2.2]-octane (which henceforth may be referred to as ABCO), and 1,4-diazabicyclo[2.2.2]-octane (which henceforth may be referred to as DABCO). These cyclic aliphatic tertiary amines, i.e., ABCO and DABCO, are more reactive initiators than DMT and other aromatic tertiary amines.

With faster polymerizations and copolymerizations, usually within seconds to minutes, comes faster set times and/or stir/stop times. The "set time" is the time it takes for the liquid starting material(s) to form a resultant tack free solid when applied to a surface. In the case of wound closure adhesives, health care providers prefer to use compositions with set times in the range of from about 30 seconds to about 120 seconds. The "stir/stop time" is the time (in seconds) stirring is stopped due to the viscosity increase of the monomer during polymerization. While stir/stop time is considered to be a more accurate measure of relative initiator activity, both the stir/stop time and set time are measures of the time it takes to convert a liquid to a solid. Like stir/stop time, the set time is from initiation of the polymerization or copolymerization (as initiation is typically commenced upon application) to completion of the reaction over the surface to be covered (e.g., wound), whereby the coating has solidified to a solid and become tack free. Thus, it will be appreciated that, while set time and stir/stop time are phenomenologically distinguishable, their definitions in polymer chemistry terms are not. It will further be appreciated that differences between quantities where "stir/stop times" were used and where "set times" were used were negligible (within experimental error). Thus, for this disclosure, reference to "set time" will be interchangeable with "stir/stop time" and both mean the same thing, i.e. the time it takes for the monomer liquid starting material(s) to form a resultant tack free, polymerized solid. Further, it is believed that the rate of crosslinking can be controlled by controlling the amount of initiator employed. The more initiator used, the faster the copolymerization and the faster the set time. In other words, the rate of copolymerization can be increased (and the set time decreased) by the addition of larger amounts of initiator.

ABCO and DABCO are crystalline solids and should be dissolved in a solvent. In at least one embodiment of the present invention, the solvent is a non-aqueous solvent. It should be recognized that, to the extent that any cyclic tertiary amine has ever been used as an initiator for any purpose whatsoever, it has always been dissolved water. In one embodiment of the present invention, the non-aqueous solvent used is tetrahydrofuran (THF). In another embodiment of the present invention, the non-aqueous solvent used is toluene. In yet another embodiment, the non-aqueous solvent is a combination of THF and toluene. In one embodiment, where application dictates, it is noted that no solvent is used.

In one or more embodiments, in addition to the initiation of the polymerization or copolymerization reaction by the cyclic tertiary amines, the step of initiating may further include further initiating the polymerization or copolymerization with nucleophilic groups located on the surface to be covered by the co-network. In one embodiment, the surface to be covered is skin.

In one or more embodiments, the method provides the use of high activity cyclic aliphatic tertiary amine initiators for cyanoacrylate polymerization, and 2-octyl cyanoacrylate and Ø(PIB-CA)$_3$ copolymerization in order to reduce the "set time" of the co-network formed from minutes (i.e., approximately 6 to 10 minutes) to seconds (i.e., less than about 120 seconds). In one embodiment, the set time is reduced to less than about 120 seconds. In another embodiment, the set time is reduced to less than 30 seconds. In another embodiment, the set time is reduced to less than 15 seconds. In yet another embodiment, the set time of the resultant poly(2-octyl cyanoacrylate) or the resultant co-networks of the present invention is shorter than the set time for poly(2-octyl cyanoacrylate) or other co-networks using an initiator other than a cyclic tertiary aliphatic amine, (e.g., an aromatic tertiary amine) under the same conditions (i.e., using the same molar concentrations of initiator in the same solvent). In one embodiment, the set time for the resultant poly(2-octyl cyanoacrylate) or the resultant co-networks of the present invention is at least 30 seconds shorter than the set time for poly(2-octyl cyanoacrylate) or other co-networks using an initiator other than a cyclic tertiary aliphatic amine (e.g., an aromatic tertiary amine), under the same conditions and using the same molar concentrations. In other embodiments, the set time for the resultant poly(2-octyl cyanoacrylate) or the resultant co-networks of the present invention is at least 60 seconds shorter than the set time for poly(2-octyl cyanoacrylate) or other co-networks using an initiator other than a cyclic tertiary aliphatic amine, under the same conditions and using the same molar concentrations, particularly where the initiators of the present invention are selected from ABCO and DABCO.

Given the significantly increased rates of polymerization or copolymerization using the initiators of the present invention, it will be appreciated that the monomer to initiator molar concentration ratios may be significantly higher than the monomer to initiator molar concentration ratios used with another initiator, particularly DMT. Necessarily, in order for any effective polymerization or copolymerization to occur with the initiator DMT, the monomer:initiator molar concentration ratio of DMT in 5 vol. % THF for 2-octyl cyanoacrylate is less than 1000:1, and more typically, less than 600:1. Again, by increasing the amount of initiator, one speeds up the reaction and provides for a reduction in set times. For example, in order to obtain a set time of about 200 seconds, the molar ratio of monomer to DMT in 5 vol. % THF would have to be about 400:1. If the DMT is in bulk, the amount of initiator would have to increase, thereby reducing the ratio to about 200:1.

In contrast, for the polymerization of 2-octyl cyanoacrylate and/or the copolymerization of 2-octyl cyanoacrylate and Ø(PIB-CA)$_3$, the monomer:initiator molar ratio concentration will be essentially at least ten-fold, or even closer to twenty-fold or more higher. That is, the molar ratio of monomer to initiator for the present invention, i.e., where the initiator is a cyclic tertiary aliphatic amine such as ABCO or DABCO, can be upwards of 20,000:1 to obtain the same set time of about 200 seconds. This is a significant decrease in the amount of initiator needed to initiate the polymerization or copolymerization reactions.

Accordingly, such co-networks are believed advantageous as wound closure adhesives, as well as sealants for other medical applications. In one embodiment, the resultant polymer or co-network is provided to form a wound closure adhesive. The mechanical properties of the resultant polymer or co-network are also significantly improved. In one embodiment, the co-network formed exhibits an elongation of at least 65%. In another or the same embodiment, the co-network formed exhibits a tensile strength of at least 3.2 MPa.

Finally, where a co-network is formed from the copolymerization reaction of 2-octyl-cyanoacrylate and a tri-telechelic star polymer comprising polyisobutylene terminated with cyanoacrylate groups (Ø(PIB-CA)$_3$), the number average molecular weight ratio of 2-octyl cyanoacrylate to Ø(PIB-CA)$_3$ can be from about 2:1 to about 9:1, wherein the polymerization reaction is initiated by at least one initiator selected from the group consisting of cyclic aliphatic tertiary amines. In other embodiments, the weight ratio is from about 2:1 to 5:1 and in still other embodiments, the weight ratio is from about 3:1 to about 4:1. Again, the cyclic aliphatic tertiary amines may be selected from ABCO or DABCO.

BRIEF DESCRIPTION OF THE DRAWINGS

FIG. 6 is a table showing the results of an experiment showing the polymerization of Oct-CA with DMT in bulk;

FIG. 7 is a table showing the results of an experiment showing the polymerization of Oct-CA with ABCO dissolved in THF;

FIG. 8 is a table showing the results of an experiment showing the polymerization of Oct-CA with DABCO dissolved in THF;

FIG. 9 is a table showing the results of an experiment showing the polymerization of Oct-CA with ABCO dissolved in Toluene;

FIG. 10 is a table showing the results of an experiment showing the polymerization of Oct-CA with DABCO dissolved in Toluene.

DETAILED DESCRIPTION OF THE INVENTION

Figure 1:
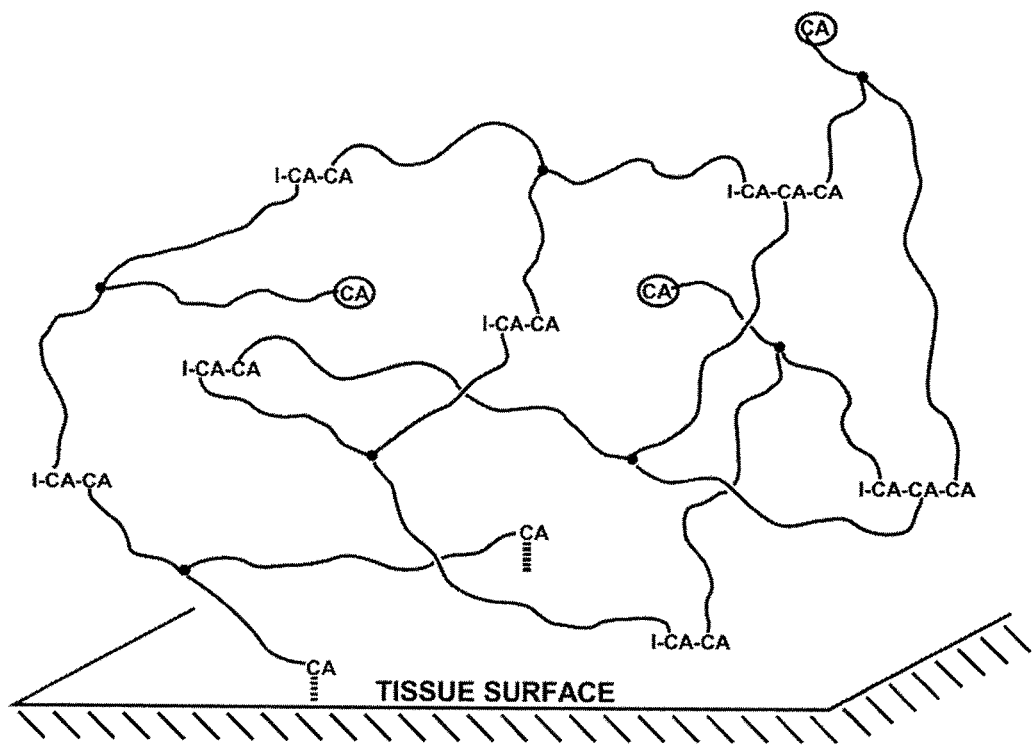
FIG. 1 is a prior art, idealized microstructure representation of a rubbery polyisobutylene homopolymer formed of Ø(PIB-CA)$_3$, wherein the CA-CA bonds are sufficiently short to only be crosslinkers.

As noted hereinabove, the present invention seeks to provide a method for increasing the rate of polymerization of 2-octyl cyanoacrylate or the rate of copolymerization of 2-octyl-cyanoacrylate (Oct-CA) and cyanoacrylate-terminated tri-telechelic polyisobutylene (Ø(PIB-CA)$_3$) to form a polymer composition or co-network composition, respectively, suitable for any of a number of biomedical applications, from wound closure and healing of skin tissue, to sealant for surgical cuts. Where the composition is a co-network, the co-network may comprise a copolymer of 2-octyl-cyanoacrylate (Oct-CA) and cyanoacrylate-terminated tri-telechelic polyisobutylene (Ø(PIB-CA)$_3$). While the polymerization of Oct-CA or the copolymerization of Oct-CA with Ø(PIB-CA)$_3$ may be initiated by the moisture (i.e., nucleophiles) within the skin, blood or other living (or dead) tissue itself when a mixture of the liquid starting materials is sprayed, coated or otherwise applied over wounds or surgical cuts, it has been found that the rate of polymerization of the Oct-CA, or the rate of copolymerization of 2-octyl-cyanoacrylate (Oct-CA) and cyanoacrylate-terminated tri-telechelic polyisobutylene (Ø(PIB-CA)$_3$) to form the co-network, can be significantly increased by the use of particular initiators applied just before application of the liquid starting materials to the skin, wound, or surgical cut.

As noted above, the starting composition is a liquid (or liquids) that can be applied by essentially any means known in the art to form a coating or film that preferably rapidly solidifies into a robust rubbery protecting barrier. In at least one embodiment, which is well known for wound closure adhesives, the liquid starting cyanoacrylate-based composition is contained or packaged within a special delivery device, wherein the composition (together with a variety of additives, modifying agents, etc.) is sealed in a thin-walled glass vial that is crushed upon deployment, and the liquid monomer(s) is then forced towards the skin through a small porous plastic sponge (typically of polypropylene or nylon) situated at the tip of the delivery port. It is generally not appreciated, but the sponge at the tip of the delivery device performs two critical functions. First, it helps evenly deliver the active ingredient over the targeted surface. Second, and perhaps more importantly, it often contains an initiator used to induce and/or accelerate the polymerization of the Oct-CA monomer(s) or the CA-terminated compounds as it is squeezed through the sponge. Absent the initiator, the set time is undesirably long, usually many minutes. For example, it has been found that the set time was less than a minute when a glass vial of a commercial Dermabond® sample was crushed and the liquid was allowed to flow, as designed, through the sponge onto a glass surface with the initiator DMT. In contrast, the set time was 8-10 minutes when the vial was crushed but the liquid spilled directly over the same surface i.e., without contacting the sponge or the initiator.

While the tissue, e.g., skin, or more accurately, the nucleophilic groups (—OH, NH2, etc.) on the surface of the skin, can, in effect, act as a "catalyst" of the polymerization, i.e., be the agent that initiates the polymerization, it has been found that using the skin will only reduce the set time by a couple of minutes, i.e. from 8-10 minutes, to 6-8 minutes. Thus, the use of the skin will aid catalyzing the reaction, but will not significantly increase the rate of polymerization or copolymerization.

Further, the polymer that forms must be a biocompatible biostable hydrophobic elastomeric barrier to bacterial invasion that keeps the coated skin moist, thereby promoting healing. The barrier, because of the specific catalyzed initiation mechanism, must adhere strongly by covalent bonds onto the surface of the tissue. Because of the absence of Ø(PIB-CA)₃ in earlier purely polyalkyl-cyanoacrylate wound closures, earlier wound closures did not exhibit such advantageous combination of elastomeric properties.

For the present invention, it has been discovered that cyclic aliphatic tertiary amines (e.g., ABCO and DABCO dissolved in dry toluene or tetrahydrofuran) very rapidly and efficiently initiate the polymerization of 2-octyl cyanoacrylate (Oct-CA) and the copolymerization of Oct-CA with three-arm star tri-telechelic polyisobutylene [Ø(PIB-CA)3], i.e., monomers useful for the preparation of wound closure adhesives.

To begin, it will be appreciated that the chemical formulas of the two starting materials are shown below as formulas (I) and (II).

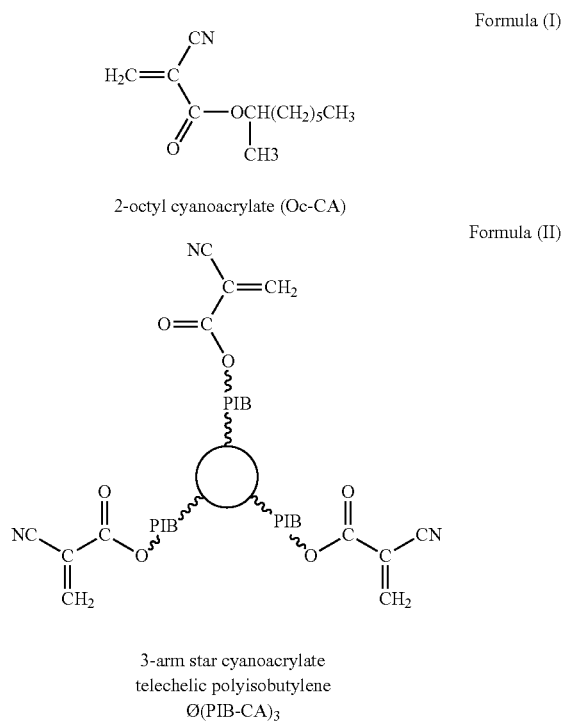

Because both Ø(PIB-CA)₃ and Oct-CA contain polymerizable cyanoacrylate (CA) groups they can readily produce polymers. Polymer (i.e., polymer or co-network) compositions can essentially be controlled by using desired amounts of the two ingredients. Overall, the co-network composition will reflect the relative composition of the starting monomers. Generally, a molar ratio of 2-octyl cyanoacrylate to Ø(PIB-CA)₃ can be from about 5:1 to about 40:1, for the copolymerization reaction, wherein the copolymerization reaction is initiated by at least one initiator selected from the group consisting of cyclic aliphatic tertiary amines. In other embodiments, the molar ratio is from about 15:1 to 35:1 and in still other embodiments, the molar ratio is from about 20:1 to about 30:1. In other embodiments, and again generally, a number average molecular weight ratio of 2-octyl cyanoacrylate to Ø(PIB-CA)₃ can be from about 2:1 to about 9:1, for the copolymerization reaction, wherein the copolymerization reaction is initiated by at least one initiator selected from the group consisting of cyclic aliphatic tertiary amines. In other embodiments, the weight ratio is from about 2:1 to 5:1 and in still other embodiments, the weight ratio is from about 3:1 to about 4:1. Again, the cyclic aliphatic tertiary amines may be selected from ABCO or DABCO.

Because both monomers, Ø(PIB-CA)₃ and Oct-CA, are liquids, their mixtures can be delivered in a number of different ways. In one embodiment, the liquids are delivered as described above as spraying or application via vial with plastic sponge tip to provide a suitable coating or film of the composition onto the desired tissue. In another embodiment, the liquids may be delivered by syringe, injecting the composition to a suitable site, again using the sponge tip. By allowing such monomer mixtures to polymerize in situ, solid rubbery plugs can form exactly where the mixture was injected, i.e., where the seal is needed. The fact that Ø(PIB-CA)₃, has a high molecular weight (Mn approximately=3000 g/mol), and Oct-CA are miscible was surprising because the very similar cyanoacrylates Methyl-, Ethyl-, and Butyl-CA are completely immiscible with (Ø(PIB-CA)₃) and, when such binary systems are mixed, they do not form a homogeneous phase but remain separate.

For a control embodiment of the present invention, a copolymerization of Ø(PIB-CA)₃ plus Oct-CA mixtures was initiated by the use of N-dimethyl-p-toluidine (DMT) initiator. Neat Ø(PIB-CA)₃+Oct-CA blends, upon contact with appropriate amounts of initiator, polymerized within seconds to minutes (i.e., from about 20 to about 300 seconds) to optically transparent strong rubbers. Co-network formation was demonstrated by stir/stop studies, and their structures and properties were characterized by a battery of techniques. Select co-networks, when deposited on fresh ventral porcine skin yielded hermetically-adhering optically clear rubbery coatings appropriate for occlusive wound closures.

In one control embodiment, the copolymerization of Ø(PIB-CA)₃ is reacted with various amounts of Oct-CA to form co-networks by the use of DMT initiator. The characterization and testing of the resultant products have been developed. The structures of the copolymerization of these Ø(PIB-CA)₃s with various proportions of Oct-CA, has been characterized and select properties of the resulting co-polymers (i.e., co-networks) studied. Extraction studies have indicated the formation of co-networks. Moreover, these copolymerizations are shown to occur fairly rapidly (i.e., approximately 20-30 seconds to 4-5 minutes). The molecular weight of the Ø(PIB-CA)₃ can be adjusted to yield moderately viscous liquids for easy deposition on surfaces. Select co-networks gave optically clear strong rubbery films hermetically adhering to the surface of ventral porcine skin suitable for occlusive skin closure adhesives.

The preparation and copolymerization of Ø(PIB-CA)₃ with various amounts of Oct-CA to form co-networks by the use of DMT initiator is provided below. The following is an example of one control for the invention only, and therefore, should not be seen as necessarily limiting the scope of the invention, the scope and spirit of the invention being set forth in the attached claims.

Synthesis of Ø(PIB-CA)₃.

The preparation of Ø(PIB-CA)₃ is well known and has been described in at least US Patent Application Publication No. US2014/0073743 A1, the disclosure of which is hereby incorporated by reference. Briefly, the synthesis involves the living polymerization of isobutylene induced by a trifunctional initiator and termination with allyltrimethylsilane. The 3-arm star allyl-terminated intermediate so obtained is converted quantitatively to the hydroxyl or bromine terminated intermediate, which is then reacted with anthracene-protected cyanoacryloyl chloride, or, preferentially, with 2-cyanoacrylic acid.

Earlier syntheses of Ø(PIB-CA)$_3$ carried out by the use of (protected) cyanoacryloyl chloride consistently gave yellow products. Efforts to remove the color (repeated precipitations, column chromatography, treatment with activated carbon) were only partially successful. The source of the discoloration is unknown (most likely due to traces of impurities associated with the use of thionyl chloride). In contrast, esterification of Ø(PIB-OH)$_3$ with anthracene-protected 2-cyanoacrylic acid gave colorless products (10). The following equation outlines this preferred method for the synthesis of Ø(PIB-CA)$_3$ (The protective anthracene group, indicated by A in the semi-circle, can be readily removed by maleic anhydride):

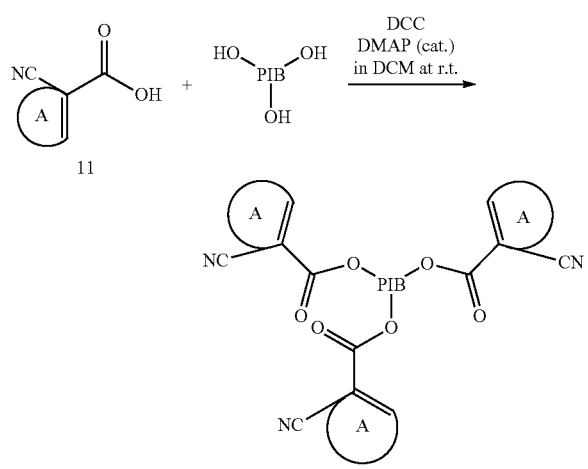

Thus, in a 50 mL Schlenk flask with a magnetic stir bar were placed under a blanket of nitrogen Ø(PIB-OH)$_3$ (1.227 g, M$_n$=2500 g/mol), anthracene-protected 2-cyano carboxylic acid adduct (1.333 g), and 4-dimethylamino pyridine (DMAP, 71.3 mg) dissolved in dichloromethane (DCM, 25 mL). Then the solution was cooled to 0° C., N,N'-dicyclohexylcarbodiimide (DCC, 1.0648 g) was added, the solution was stirred for 30 min at 0° C., and then overnight at room temperature. The precipitated urea was filtered off, the DCM was evaporated in vacuo, and the viscous residue was dissolved in THF and purified by two precipitations into methanol.

Finally, to yield Ø(PIB-CA)$_3$, the protective anthracene group was removed by treatment with maleic anhydride in refluxing xylene for 8 hrs. According to NMR analysis the yields of protection and deprotection were typically ~60 and ~90%, respectively. Similar yields have been obtained by others who used the same protection/deprotection technique.

Polymerization of Oct-CA in Bulk

A 5 ml vial containing a Teflon coated small (1 cm) magnetic stir bar was charged with Oct-CA (1.0 g), and a calculated amount of DMT initiator was injected by a micro syringe. The charge turned yellow immediately upon DMT addition due, without being bound by theory, to possibly charge complexes. The vial was capped, vigorously mixed for a few seconds, and placed on a stirring plate for stirring at ~60 rpm. The gel time, i.e., the time (in seconds) stirring stopped due to the viscosity increase and gel formation, was recorded. The instant the gel formed the yellow color disappeared and the charge became colorless.

Polymerization of Oct-CA with DMT Diluted with THF.

Polymerizations were carried out under UHP nitrogen in 50 mL Schlenk flasks equipped with a magnetic stir bar. Flasks were sealed with a rubber septum, purged with nitrogen, flame dried, cooled to room temperature and charged with Oct-CA (1.938 g, 9.26 mmol).

Polymerizations were initiated by injecting DMT (0.1224 g, 0.905 mmol) dissolved in THF (4.9 mL) under a blanket of N$_2$ at r.t. (M$_0$/I$_0$=10, [Oct-CA]=1.32 mol/L). To keep the [M]$_0$/[I]$_0$ ratio constant, the volumes of Oct-CA (0.5-1.2 mL), and initiator solutions (5-100 μL) were adjusted. The polymerization mixture became yellow immediately upon DMT addition. After about 10 minutes stirring, the yellow color disappeared, and the mixture became colorless. After overnight stirring at room temperature the colorless polymer was purified by three precipitations in methanol and dried in vacuum at 60° C. for 24 hours to constant weight.

Copolymerization of Ø(PIB-CA)$_3$ with Oct-CA

Co-networks were prepared by copolymerizing Ø(PIB-CA)$_3$ plus Oct-CA at room temperature. Thus, in a well-dried 10 mL screw-cap vial was placed Ø(PIB-CA)$_3$ (0.3-1.2 g, M$_n$=2500 or 6500 g/mol) dissolved in freshly distilled THF (3 mL). Polymerizations were induced by adding various amounts (5-150 μL) of DMT initiator. The vial was capped, the solution was vigorously manually agitated for 1-2 seconds and rapidly poured into a 7×7 cm Teflon mold. The volatiles were evaporated in a fume hood for 1 h, and the film was dried at 60° C. to constant weight.

Polymerization of Oct-CA to Thermoplastics

It will be appreciated that the repeat structure of poly(Oct-CA) is shown below as Formula (III).

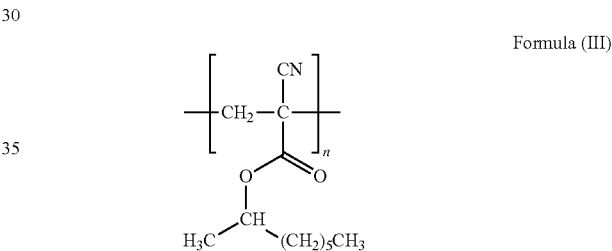

Formula (III)

Poly(Oct-CA) is an optically transparent rather stiff thermoplastic (T$_g$~58° C., see FIGS. 8 and 9), with high permanent set and a strong tendency to creep (see FIG. 7). Thus, poly(Oct-CA) tends to slough off the skin rather rapidly after deployment. Due to its stiffness it is not used over moving or creased skin.

Polymerization of Ø(PIB-CA)$_3$ to Rubbery Networks

Ø(PIB-CA)$_3$ upon contact with nucleophiles (initiators, proteinaceous tissue, moisture) crosslinks and yields networks. It has been determined that the extent and rate of crosslinking depend on a number of factors, including the length (molecular weight) of the PIB arms (i.e., the molar concentration of CA groups), and the nature and quantity of the initiator employed. The amount of extractables obtained with a representative PIB-based homo- and co-networks prepared with Ø(PIB-CA)$_3$ of M$_n$=2400 g/mol using DMT initiator was determined. The small amounts of extractables (3-5%) indicate extensive network formations.

Copolymerization of Oct-CA with Ø(PIB-CA)$_3$ to Rubbery Co-Networks

Prior to bulk copolymerizations, the mutual miscibility of Oct-CA and Ø(PIB-CA)$_3$ was investigated. It was found that Oct-CA plus Ø(PIB-CA)$_3$ having a number average molecular weight of 2500 g/mol or more (M$_n$=at least 2500 g/mol) yield optically clear blends in all proportions, indicating that Oct-CA and Ø(PIB-CA)$_3$ are miscible. In contrast, even small amounts (~5%) of Me- and Et-CA are immiscible with Ø(PIB-CA)₃ and yield hazy mixtures under the same conditions. Further, it was found that Oct-CA plus Ø(PIB-CA)₃ of $M_n$=6,500 g/mol produce hazy mixtures, indicating that the higher molecular weight Ø(PIB-CA)₃ is immiscible or only partially miscible with Oct-CA Upon the addition of 10 wt % THF to the hazy Oct-CA/Ø(PIB-CA)₃ ($M_n$=6,500 g/mol) mixture, the system became optically clear, indicating miscibility in THF solution.

Stress-strain profiles of a poly(Oct-CA), a homonetwork made by crosslinking Ø(PIB-CA)₃, and several representative co-networks of Ø(PIB-CA)₃/Oct-CA were prepared. Importantly, the stress-strain profile of poly(Oct-CA) is fundamentally different from the homo- and co-networks. While poly(Oct-CA) presents a stiff relatively weak (barely 1 MPa) thermoplastic exhibiting high permanent set (~300%), the homo- and co-networks are rubbery. The homonetwork obtained (with DMT initiator) with Ø(PIB-CA)₃ of $M_n$=2400 g/mol shows low tensile strength and elongation, however, these properties increase upon Oct-CA incorporation. Specifically, a 25/75 Ø(PIB-CA)₃ ($M_n$=6500 g/mol)/Oct-CA co-network shows a yield point at ~10% strain, after which it exhibits impressive rubbery properties with ~6 MPa tensile strength and ~180% elongation. These properties are comfortably in excess of those required of a wound closure adhesive.

Moreover, tan δ of both products show two $T_g$s, a low temperature transition corresponding to PIB (~-20 and -10° C.) and a high temperature peak due to poly(Oct-CA) sequences (~60 and ~70° C.). The $T_g$s attributed to PIB are higher than values usually reported for this polymer (i.e., ~-50 to -70° C.) because of the relatively low molecular weight PIB in the co-networks. It is noted that the $T_g$s due the poly(Oct-CA) are significantly higher than those (~40° C.) reported by earlier investigators. The E' trace of the 25% Ø(PIB-CA)₃($M_n$=2400 g/mol)/75% Oc-CA co-network shows a well-defined low and a high temperature flow region separated by a rubbery plateau, which reflect the thermal transitions. The co-network prepared with the linear CA-PIB-CA also exhibits similar trends.

Efforts to carry out DMT experiments with poly(Oct-CA) were unsuccessful because the glassy samples broke at ~-95° C.

Polymer Chemical Considerations

Since the inherent reactivity of a functional group (in this instance, the CA group) is independent of the molecular weight of the polymer it is attached to, it may be safely assumed that the reactivities of the CA groups of Oct-CA and Ø(PIB-CA)₃ are essentially identical (i.e., their reactivity ratios are unity). Thus, the compositions of co-networks are controllable by controlling the relative amounts of Oct-CA and Ø(PIB-CA)₃ in these miscible charges.

In the presence of a stoichiometric excess of Oct-CA in a Oct-CA/Ø(PIB-CA)₃ charge assembled for the synthesis of co-networks, initiation will preferentially involve Oct-CA. The first event of initiation is likely the direct addition of the initiator to Oct-CA as follows:

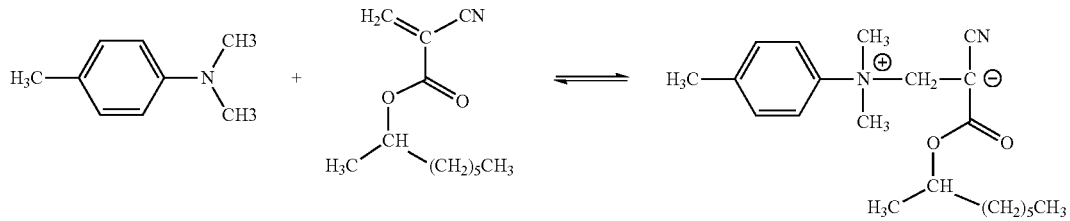

If this were true, the polymer ought to carry the initiator head group. A search of the prior art was not able to identify any reference that provided for aromatic or cyclic head groups in polymers prepared with aromatic tertiary amines (e.g., DMT) or cyclic tertiary amines. In spite of extensive research in this field by earlier workers, the exact details of initiation of anionic alkyl cyanoacrylate polymerization remain unknown.

During the early stages of polymerization the viscosity of the system is relatively low and propagation, i.e., the attack of the first CA anion to Oct-CA and/or Ø(PIB-CA)₃ (that yields crosslinking) is relatively unhindered as set forth in the reaction scheme below:

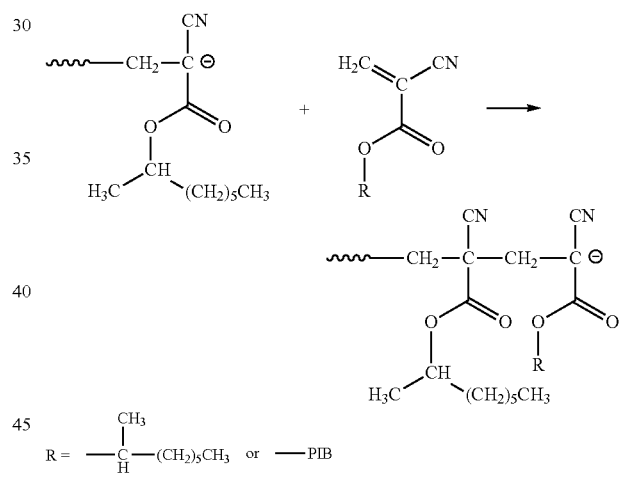

Upon further propagation steps, particularly after Ø(PIB-CA)₃ incorporation, the viscosity of the system rises very rapidly and the rate of (co)polymerization necessarily drops precipitously. Ultimately, a fraction of CA groups likely become entrapped in the highly viscous matrix and propagation ceases.

Due to the highly hydrophobic matrix, termination, i.e., the permanent annihilation of propagating anions, which likely involves reaction with protons (i.e., moisture), is absent or is very slow in these bulk polymerizations. The mechanical properties of the products may be controlled by controlling the relative proportions of the rubbery PIB and glassy poly(Oct-CA) segments. By increasing the length of the PIB arms, elongations increase and moduli decrease. The longer poly(Oct-CA) sequences would phase separate and may function as reinforcing sites. Ultimate properties could also be controlled by the use of mixtures of two (or more) Ø(PIB-CA)₃s of different $M_n$s, or blends of Ø(PIB-CA)₃s with linear telechelic CA-PIB-CAs.

Microstructure/Morphology

FIG. 1 shows an idealized microstructure of a prior art network formed by the polymerization of Ø(PIB-CA)$_3$ deposited on a proteinaceous surface (skin). These constructs are in fact PIB networks (the CA groups merely provide initiating and crosslinking sites) with two kinds of crosslinking sites: (a) the aromatic centers of the Ø(PIB-CA)$_3$, and (b) crosslinks formed by linking two (or less likely, three) CA groups. Polymerizations may be induced by the initiator (I) (where the initiator is DMT), nucleophilic groups on the surface of the skin, or adsorbed moisture. The networks are expected to contain numerous loops and catenates, which affect ultimate load bearing properties. In FIG. 1, the wiggly lines are PIB, I is the initiator, ● is the aromatic center of Ø(PIB-CA)$_3$, CA--- is the cyanoacrylate available for bonding or bonded to the skin surface, the CA-CA with the I initiator are the formed crosslinkers for the network, and the CAs in circle are "useless" entrapped CA). The loops and entrapped/catenated crosslinks are to be noted.

Figure 2:
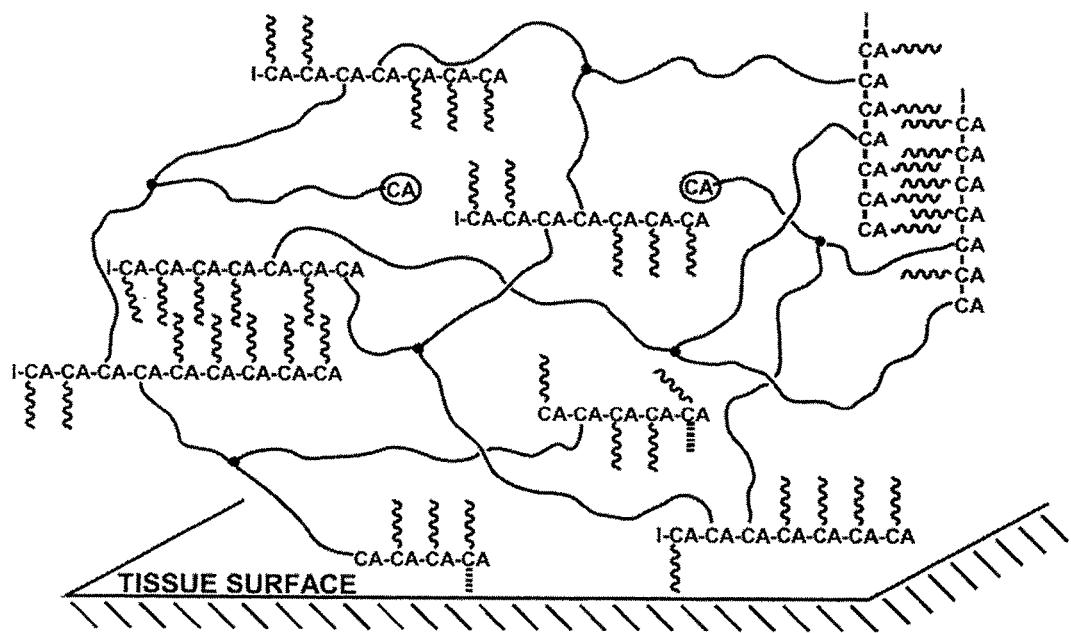
FIG. 2 is an idealized microstructure representation of a polyisobutylene co-network that arises from a homogeneous 50/50 wt/wt polymer blend of Oct-CA plus Ø(PIB-CA)$_3$ upon the addition of an initiator at room temperature, wherein the poly(Oct-CA) sequences polymerized are of sufficient length (i.e., greater than 3 CA units) to form separate coalesced phases whose T$_g$ can be identified by appropriate instrumentation such as DSC or DMTA.

With more particular respect to the present invention, FIG. 2 shows an idealized microstructure of a co-network that arises from a homogeneous 50/50 wt/wt blend of Oct-CA plus Ø(PIB-CA)$_3$ upon the addition of an initiator at room temperature. In these co-networks, the poly(Oct-CA) sequences are of sufficient length (i.e., greater than 3 CA units) to form separate coalesced phases whose $T_g$ can be identified by appropriate instrumentation. As shown in FIG. 2, the 50/50 wt/wt Poly[Oc-CA-co-Ø(PIB-CA)$_3$] co-network is represented, with the wiggly lines being PIB, I being the initiator, CA--- being the Oct-CA bonded to or available for bonding to the skin surface, The CA of multiple units being the Poly(Oct-CA), the CAs in the circle being "useless" CA groups entrapped in matrix, and the ● being the aromatic center of Ø(PIB-CA)$_3$. Again the presence of catenated/entrapped crosslinks and PIB loops should be noted. Importantly, the polymerization of CA groups is initiated by a purposely added initiator (I), in addition to a nucleophilic group (N or O) in the epidermis (---), or by traces of moisture (not shown).

In light of the foregoing, it will be appreciated that, depending upon the number of CA units, either neat Ø(PIB-CA)$_3$, or Oct-CA plus Ø(PIB-CA)$_3$ blends, upon contact with an initiator, produce rubbery homo-networks or co-networks, respectively, of potential use as occlusive flexible wound closure adhesives. A variety of such networks have been prepared, characterized by various techniques, and select properties, e.g., elongation, tensile strength, have been determined. Viscous blends of starting materials upon contact with appropriate amounts of initiator polymerize within a few seconds to minutes and produce rubbery strongly adherent transparent coatings on skin. The coatings follow the contours and irregularities of the skin, giving rise to smooth rubbery flexible transparent membranes, which adhere strongly to the surface and provide seamless hermetic closures.

The rubbery character (stretchiness) of the co-network can be increased by increasing the concentration of the Ø(PIB-CA)$_3$ in the co-network. Other properties can be controlled by controlling the molecular weights (Mn) of the co-network segments (i.e., the number average molecular weights of the poly(Oct-CA) and Ø(PIB-CA)$_3$, respectively). While any molecular weight range can be used, one suitable range would be to provide the molecular weight of poly(Oct-CA) as from about 3000 g/mol to 5000 g/mol, with about 4000 g/mol being suitable for one embodiment, and that of Ø(PIB-CA)$_3$ being from about 2000 g/mol to about 4000 g/mol, with about 3000 g/mol being suitable in one embodiment. Thus, it will be appreciated that, for the three arm tri-telechelic cyanoacrylate PIBs, each PIB arm is about 1000 g/mol. The production of these two starting molecules is well known to those of skill in the art.

In order to demonstrate practice of the present invention, various polymerizations and copolymerizations were conducted which were initiated with DMT (control), ABCO, and DABCO. The following exemplified procedure and results are provided to show a detailed example of the present invention. Therefore, it should not be seen as narrowing the invention, breadth and spirit of the invention being dictated by the attached claims.

Materials

N,N-dimethyl-p-toluidine (DMT, 99%), purchased from Aldrich, was used as received. Azabicyclo[2.2.2]-octane 97+% (ABCO), and 1,4-diazabicyclo[2.2.2]-octane 98% (DABCO) were purchased from Alfa Aesar and were used without further purification. Ethyl-2-cyanoacrylate (Et-CA) was purchased from Loctite, and 2-octyl cyanoacrylate (Oct-CA) was purchased from Chenso, and they were used without further purification. Tetrahydrofuran, purchased from Aldrich and toluene were thoroughly dried by refluxing and distilling the solvents over sodium and benzophenone.

Instruments and Procedures

Proton ($^1$H) NMR spectroscopy, (Varian Gemini 300 and 500 MHz instruments and deuterated chloroform as solvent) was used to determine chemical structures, chain-end functionalities and molecular weights ($M_n$).

Gel permeation chromatography (GPC) eluograms were obtained using a Waters GPC instrument equipped with a series of three Waters Styragel-HR columns (HR-1, HR-4E, HR-5E), a refractive index detector (Waters 2414) and a multiangle laser light scattering detector (Dawn EOS, Wyatt Technology). Samples were dissolved in THF, the flow rate was 1 mL THF/min, and column temperature was 35° C.

Stress strain properties of microdumbell-shaped samples were determined with a Texture Analyzer TA.XTplus tester with a 5 kilo load cell at a crosshead speed of 5 mm/min, following ASTM D638-02a. Samples (0.2-0.25 mm thick) were punched from solution (THF) cast films.

Syntheses and Chemical Manipulations-Synthesis of Ø(PIB-CA)$_3$

Figure 3A:
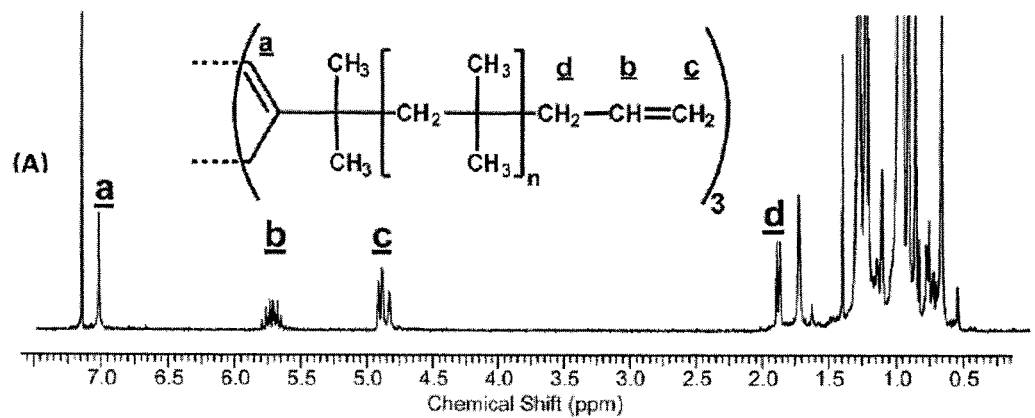
FIG. 3A is the H NMR spectrum of an allyl three-arm star PIB intermediate.
Figure 3B:
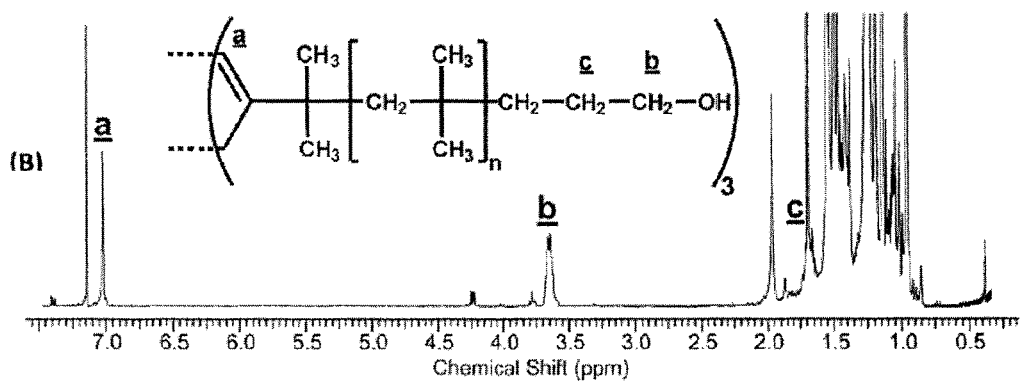
FIG. 3B is the H NMR spectrum of a hydroxyl-three arm star PIB intermediate.
Figure 3C:
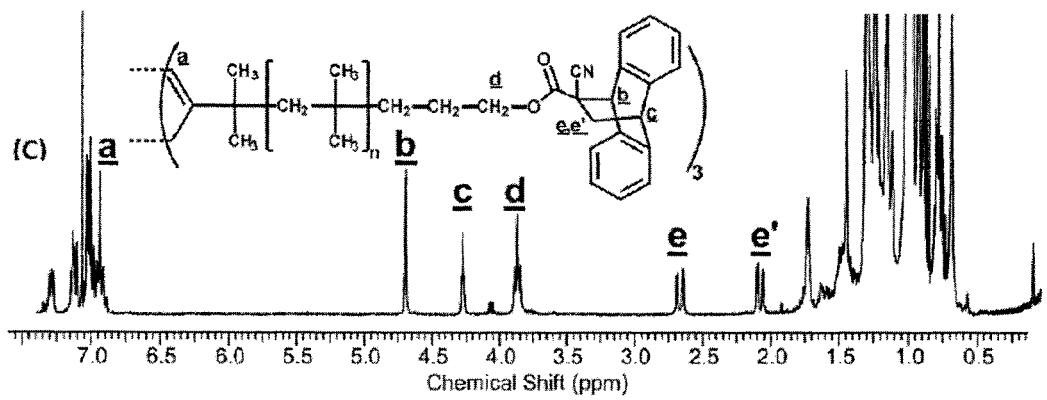
FIG. 3C is the H NMR spectrum of an anthracene/cyanoacrylate adduct three arm star PIB intermediate.
Figure 3D:
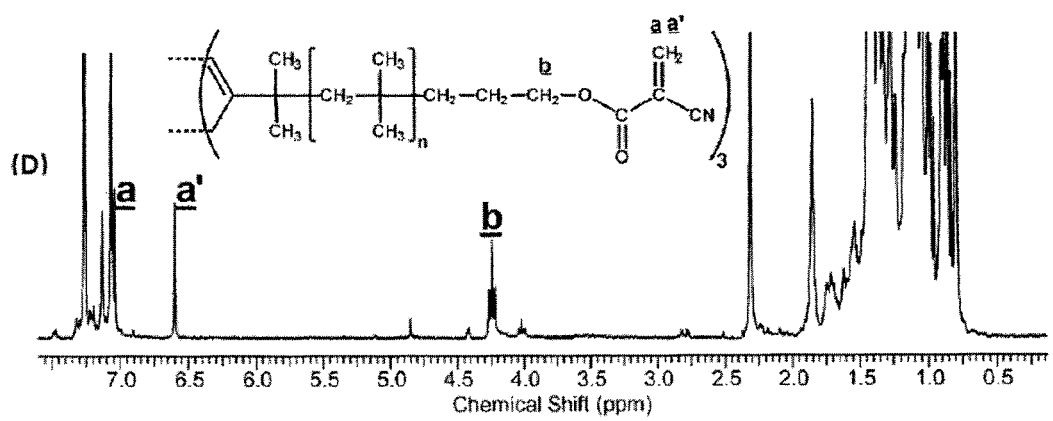
FIG. 3D is the H NMR spectrum the cyanoacrylate-tri-telechelic PIB, Ø(PIB-CA)$_3$ final product.

The synthesis started with the living polymerization of isobutylene induced by a trifunctional initiator, and the polymerization was terminated with allyltrimethyl silane. The 3-arm star allyl-terminated intermediate was converted quantitatively to a hydroxyl terminated intermediate, which was then reacted with anthracene-protected acryloyl chloride. Finally, the protective anthracene group was removed by treatment with maleic anhydride in refluxing xylene for about 10 hours to yield the target Ø(PIB-CA)$_3$. FIGS. 3A-3C show the NMR spectra of the intermediates (allyl-, hydroxyl-, and anthracene/cyanoacrylate adduct) and FIG. 3D shows the NMR spectra of the final product (cyanoacrylate-tri-telechelic PIBs, Ø(PIB-CA)$_3$).

Figure 4:
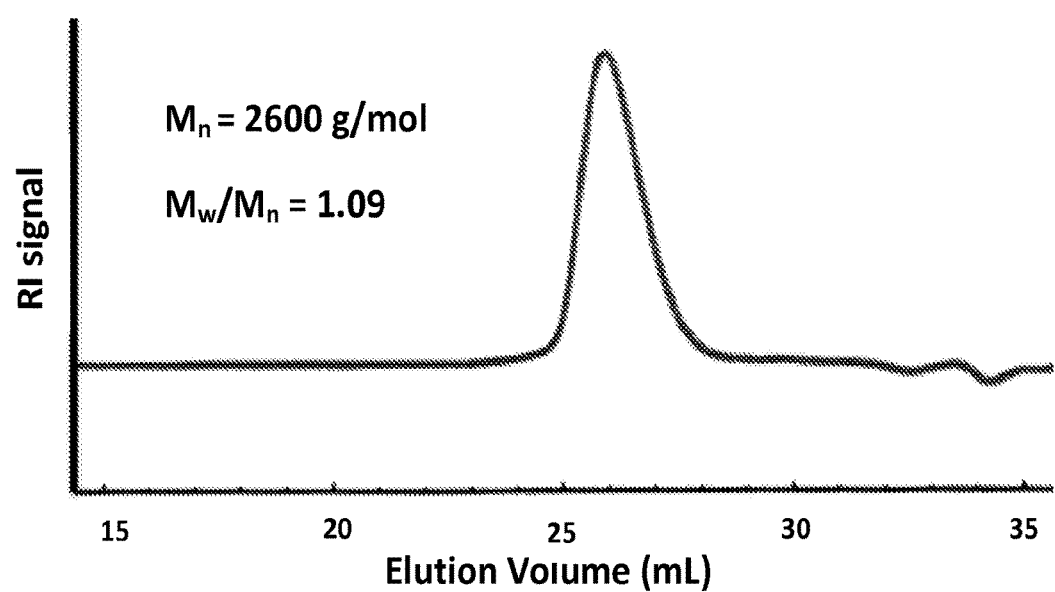
FIG. 4 is the GPC trace of a representative three-arm star allyl-tri-telechelic polyisobutylene.

FIG. 4 displays the GPC trace of the first intermediate (allyl-), indicating the presence of a homogenous well-defined material with narrow molecular weight dispersity. The GPC traces of the other intermediates were similarly narrow.

Polymerization of Oct-CA in Solution

Figure 5:
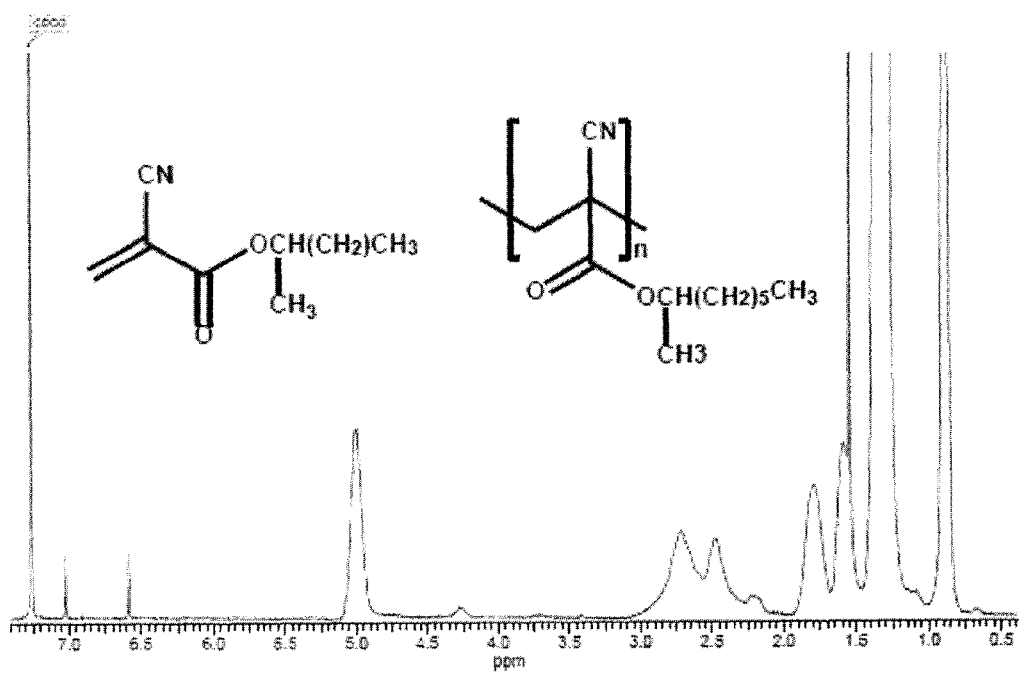
FIG. 5 is a Proton NMR spectrum of Poly(Oct-CA)

The polymerization was carried out in a 50 mL Schlenk flask equipped with a magnetic stir bar under UHP nitrogen. The flask was sealed with a rubber septum and purged with nitrogen and flame dried. Then 1.938 g (9.26 mmol) Oct-CA was placed in the flask and the polymerization started by injecting a DMT initiator (0.1224 g, 0.905 mmol, dissolved in 4.9 mL THF) under $N_2$ (t=0); $M_0/I_0$=10, [Oct-CA]=1.32 mol/L. After about 8 hours of stirring at room temperature, the system was precipitated into methanol and dried in a vacuum at 60° C. overnight. FIG. 5 shows the H NMR spectrum.

Polymerization of Ø(PIB-CA)$_3$ and Copolymerization of Ø(PIB-CA)$_3$ with Oct-CA Networks were prepared by polymerizing Ø(PIB-CA)$_3$ and co-networks by copolymerizing Ø(PIB-CA)$_3$ plus Oct-CA at room temperature. Thus, in a well-dried 10 mL screw-cap vial was placed Ø(PIB-CA)$_3$ (0.3-1.2 g, $M_n$=2500 or 6500 g/mol) dissolved in 3 mL freshly distilled THF. Polymerizations were induced by adding various amounts (5-150 µL) of the initiator (DMT in bulk, [ABCO]=0.0042 mol/L, or [DABCO]=0.0045 mol/L) dissolved in THF to the monomer solution. The vial was capped; the solution was briefly vigorously manually mixed, and then rapidly poured into a 7×7 cm Teflon mold. The volatiles were evaporated in a fume hood for 1 hour, and the film was dried at 60° C. to constant weight.

Copolymerizations were carried out similarly, except desired amounts of Oct-CA were added to the Ø(PIB-CA)$_3$. It is important to note that while Me- and Et-CA are immiscible, Oct-CA is miscible with Ø(PIB-CA)$_3$ of Mn=2500 g/mol, and the latter blends are optically clear. In contrast, Oct-CA plus Ø(PIB-CA)$_3$ of Mn=6,500 g/mol yielded hazy mixtures, indicating that the higher molecular weight Ø(PIB-CA)$_3$ is immiscible with Oct-CA Upon the addition of 10 wt % THF to the latter mixture, the Ø(PIB-CA)$_3$ (Mn=6,500 g/mol)/Oct-CA system becomes optically clear, which indicates miscibility.

Relative Initiator Reactivities

The relative reactivity of various initiators was assessed by determining the time (in seconds) that a well-defined weight of liquid Oct-CA could be stirred after adding to it a well-defined amount (in moles) of initiator at room temperature. Thus, 1 g Oct-CA and a Teflon coated small (1 cm) magnetic stir bar were placed in a 5 mL screw cap vial. At time=0 a known amount of initiator (in some instances dissolved in toluene or THF) was injected into the monomer by means of a Hamilton syringe, the vial was capped and stirring (about 60 rpm, stirring plate) was started. The gel time, i.e., the time (in seconds) stirring stopped due to the viscosity increase of the monomer, was determined, and is considered to be a measure of relative initiator activity. Both the gel time and set time are measures of the rate of crosslinking, i.e., the time it takes to convert a liquid to a solid.

EXAMPLES

The experiments began using DMT, a readily available aromatic tertiary amine, frequently used as an efficient initiator for the polymerization of CAs. In the course of this work it was hypothesized that cyclic aliphatic tertiary amines, e.g., ABCO and DABCO, would be more reactive initiators than DMT (or pyridine, or other frequently used tertiary amines) due to the presence of more available, less encumbered ring N atoms in these cyclic tertiary amines. While the dangling substituents attached to N in DMT are expected to sterically hinder the approach of monomer during initiation, the substituents on N in ABCO or DABCO are forced out-of-the-way so that initiation becomes less hindered, and consequently faster. The formulas help to visualize the substituent groups on the N in these tertiary amines:

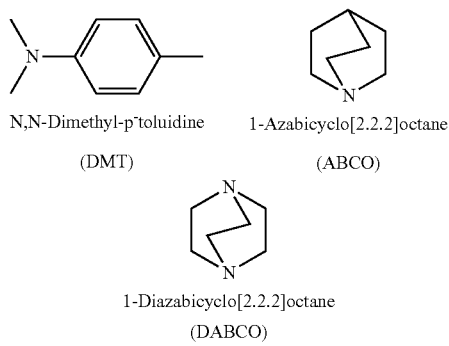

N,N-Dimethyl-p-toluidine (DMT)

1-Azabicyclo[2.2.2]octane (ABCO)

1-Diazabicyclo[2.2.2]octane (DABCO)

Faster initiation would desirably shorten set times, and thus the rate of crosslinking could be controlled by controlling (and hopefully, reducing) the amount of the initiator employed.

FIGS. 6-11 summarize the results of a series of experiments whose aim was to assess the relative initiating efficiency of DMT (the control), and ABCO and DABCO for the polymerization of Oct-CA. Other initiators, namely triethylamine and pyridine, were also tested. Neither triethylamine nor pyridine are cyclic aliphatic tertiary amines. Pyridine is aromatic, while triethylamine is not cyclic. While DMT is a liquid and can be blended as such with the liquid monomer, ABCO and DABCO are crystalline solids and thus have to first be dissolved in a solvent (e.g., toluene or THF) to be administered. The data also shows the effect on the rate of the use of small amounts of toluene and tetrahydrofuran in conjunction with ABCO, DABCO, pyridine, and DMT. This solvent requirement in conjunction with ABCO and DABCO led to a further discovery in regard to the effect of solvent polarity on the rate of Oct-CA polymerization.

Figure 11:
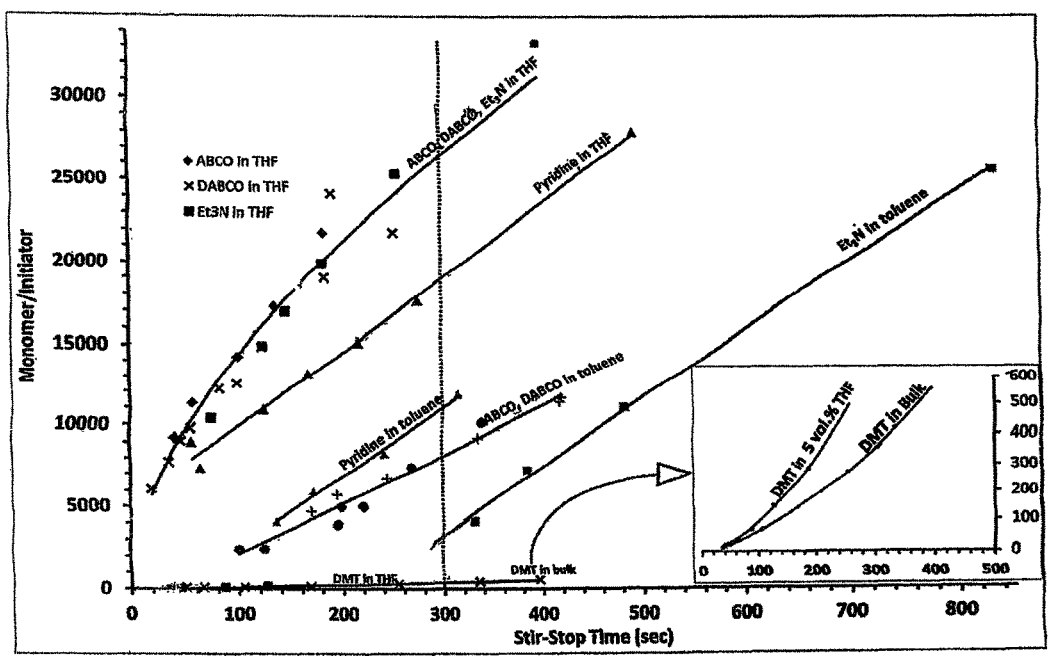
FIG. 11 shows the relationship between the [Monomer]/[Initiator] Ratio and Stir/Stop Times for the experiments shown in FIGS. 6-10.

The desirable range of set times is between 20 and 120 seconds. As shown in the inlay of FIG. 11, the bulk polymerization of Oct-CA induced by the well-known DMT initiator (the control) requires relatively large initiator concentrations (relatively low monomer/initiator ratios on the order of a molar ratio of about 50:1 to about 100:1) for efficient polymerization within the desired set time, and lesser amounts of initiator results in much longer set times. In this system a solvent is not needed to mix the initiator and the monomer because these liquids ingredients are miscible. Heat is generated upon mixing the DMT initiator with Oct-CA and, depending the amount of DMT used, the temperature of the system can rapidly rise to 50-70° C. The Oct-CA+DMT system exhibits a significant induction period (about 60 seconds) before rapid polymerization starts. During this induction period the liquid ingredients have time to mix thoroughly. After the induction period the viscosity of the system rapidly increases and conversions reach 90-95% within seconds. Conversions were determined by FTIR spectroscopy measuring the extent of monomer (unsaturation) remaining in the system. The poly(Oct-CA) that is forming is soluble in the monomer so the polymerization is homogeneous. The Oct-CA+DMT mixture is yellow, however the color disappears the instant a semisolid colorless transparent polymer product arises.

As further shown in the inlay of FIG. 11, the polymerization of Oct-CA induced by the well-known DMT initiator in vol. 5% THF (the control) also requires relatively large initiator concentrations (relatively low monomer/initiator ratios on the order of a molar ratio of about 50:1 to about 200:1) for efficient polymerization within the desired set time, and lesser amounts of initiator results in much long set times. As compared to DMT in bulk, the rate of polymerization is faster as lesser amounts of initiator is used, but still the amount of initiator is relatively high (i.e. greater than 600:1).

As clearly indicated by the data in FIG. 11, the polymerizations induced by ABCO and DABCO are much faster (monomer/initiator ratios are much larger and set times [shown as "Stir-Stop Time" in the figure] much shorter) than those induced by DMT. The rates are also strongly affected by the nature of the solvent used to dissolve these aliphatic cyclic amines. Thus, polymerizations induced by ABCO and DABCO dissolved in THF were much faster than those in which toluene was used as initiator solvent. This effect is most likely due to faster initiation in the more polar THF, i.e., due to the formation of THF-solvated propagating ions from the neutral starting materials. The dielectric constant of THF is significantly higher than that of toluene.

In reviewing FIG. 11, it will be appreciated that the polymerization of 2-octyl cyanoacrylate and/or the copolymerization of 2-octyl cyanoacrylate and Ø(PIB-CA)$_3$ induced by ABCO and DABCO are fast (on the order of less than 10 seconds to about 300 seconds depending upon the monomer-initiator ratio employed). Furthermore, the monomer-initiator molar ratio concentration will be essentially at least ten-fold, or even closer to twenty-fold or higher. That is, the molar ratio of monomer to initiator for the present invention, i.e., where the initiator is a cyclic tertiary aliphatic amine such as ABCO or DABCO in toluene solvent, can be upwards of 2,000:1 to obtain the same set time of about 100 seconds. Even more impressive is that the molar ratio of monomer to initiator for the present invention, i.e., where the initiator is a cyclic tertiary aliphatic amine such as ABCO or DABCO in THF solvent, can be upwards of 12,000:1 to obtain the same set time of about 100 seconds. This is a significant decrease in the amount of initiator needed to initiator the polymerization or copolymerization reactions.

In light of the foregoing, it will be appreciated that ABCO and DABCO are efficient super-initiators not only for the homopolymerization of Oct-CA, but also for the copolymerization of Oct-CA with CA-telechelic polyisobutylenes, e.g., three-arm star CA-terminated PIB [Ø(PIB-CA)$_3$]. These co-networks are useful rubbery wound closure adhesives. The rate of these copolymerizations can be significantly increased and the set times of these wound closure adhesives can be significantly shortened, by the use of ABCO or DABCO.

What is claimed is:

1. A method for increasing the rate of polymerization of 2-octyl cyanoacrylate, or the rate of copolymerization of 2-octyl cyanoacrylate and a tri-telechelic star polymer comprising polyisobutylene terminated with cyanoacrylate groups (Ø(PIB-CA)$_3$) to form a co-network, the method comprising:
   initiating the polymerization of 2-octyl cyanoacrylate, or the copolymerization of 2-octyl cyanoacrylate and Ø(PIB-CA)$_3$ to form the co-network, with an initiator selected from the group consisting of cyclic tertiary aliphatic amines optionally dissolved in a non-aqueous solvent, wherein the cyclic tertiary aliphatic amines are selected from the group consisting of azabicyclo[2.2.2]-octane (ASCO), and 1,4-diazabicyclo[2.2.2]-octane (DABCO).

2. The method according to claim 1, wherein the non-aqueous solvent is used and is selected from the group consisting of tetrahydrofuran (THF), toluene, and combinations thereof.

3. The method according to claim 1, wherein the step of initiating further includes further initiating the polymerization or copolymerization with nucleophilic groups located on the surface to be covered by the co-network.

4. The method according to claim 3, wherein the surface to be covered is skin.

5. The method according to claim 1, wherein the polymerization of 2-octyl cyanoacrylate is provided, and wherein a set time for the resultant poly(2-octyl cyanoacrylate) is shorter than the set time for formation of poly(2-octyl cyanoacrylate) from the polymerization of 2-octyl cyanoacrylate using an aromatic tertiary amine initiator in the same solvent and initiator concentration.

6. The method according to claim 1, wherein the copolymerization of 2-octyl cyanoacrylate and Ø(PIB-CA)$_3$ is provided, and wherein a set time for the resultant 2-octyl cyanoacrylate-Ø(PIB-CA)$_3$ co-network is shorter than the set time for formation of a like co-network from the copolymerization of 2-octyl cyanoacrylate and Ø(PM-CA)$_3$ using an aromatic tertiary amine initiator in the same solvent and initiator concentration.

7. The method according to claim 5, wherein the non-aqueous solvent is present and is THF.

8. The method according to claim 1, wherein the molar ratio of monomer to initiator is greater than 1000:1 and the set time is less than 300 seconds.

9. The method according to claim 8, wherein the set time is less than 120 seconds.

10. The method according to claim 5, wherein the set time for the resultant poly(2-octyl cyanoacrylate) is at least 30 seconds shorter than the set time for poly(2-octyl cyanoacrylate) using an aromatic tertiary amine initiator in the same solvent and initiator concentration.

11. The method according to claim 10, wherein the set time for resultant poly(2-octyl cyanoacrylate) is at least 60 seconds shorter than the set time for poly(2-octyl cyanoacrylate) using an aromatic tertiary amine initiator in the same solvent and initiator concentration.

12. The method according to claim 6, wherein the set time for the resultant co-network is at least 30 seconds shorter than the set time for other co-networks using an aromatic tertiary amine initiator in the same solvent and initiator concentration.

13. The method according to claim 12, wherein the set time for the resultant co-network is at least 60 seconds shorter than the set time for other co-networks using an aromatic tertiary amine initiator in the same solvent and initiator concentration.

* * * * *